United States Patent
Bornzin

[11] Patent Number: 5,891,176
[45] Date of Patent: Apr. 6, 1999

[54] SYSTEM AND METHOD FOR PROVIDING HEMODYNAMICALLY OPTIMAL PACING

[75] Inventor: Gene A. Bornzin, Simi Valley, Calif.

[73] Assignee: Pacesetter, Inc., Sylmar, Calif.

[21] Appl. No.: 736,891

[22] Filed: Oct. 25, 1996

Related U.S. Application Data

[60] Provisional application No. 60/082,419 May 9, 1996.

[51] Int. Cl.⁶ .................................................. A61N 1/368
[52] U.S. Cl. ............................................................ 607/18
[58] Field of Search ................................ 601/17, 18, 19, 601/23–25, 27

[56] References Cited

U.S. PATENT DOCUMENTS

| | | |
|---|---|---|
| 5,024,222 | 6/1991 | Thacker . |
| 5,312,452 | 5/1994 | Salo ........................................... 607/17 |
| 5,330,511 | 7/1994 | Boute ......................................... 607/17 |
| 5,466,245 | 11/1995 | Spinelli et al. ............................ 607/17 |
| 5,487,752 | 1/1996 | Salo et al. ................................. 607/17 |
| 5,540,727 | 7/1996 | Tockman et al. ......................... 607/17 |
| 5,549,650 | 8/1996 | Bornzin et al. ........................... 607/24 |

*Primary Examiner*—William E. Kamm
*Assistant Examiner*—George R. Evanisko

[57] ABSTRACT

A system and method for a pacemaker are provided, for monitoring cardiac performance and adjusting a pacing regime to ensure hemodynamically optimal pacing therapy. The pacemaker includes a sensor for measuring a physiological parameter as an indicator of cardiac performance. A processing system dithers various programmable pacing parameters and notes the resulting changes in cardiac performance. The processor analyzes the changes in cardiac performance corresponding to changes in the pacing parameters and selects those parameters resulting in maximum cardiac performance. An activity sensor may be provided to allow the processing system to consider the activity level of a patient when determining a hemodynamically optimal pacing regime.

24 Claims, 4 Drawing Sheets

SYSTEM AND METHOD FOR PROVIDING HEMODYNAMICALLY OPTIMAL PACING

This application claims the benefit of U.S. Provisional Application No. 60/082,419 filing date May 9, 1996.

FIELD OF THE INVENTION

This invention relates to implantable cardiac stimulation devices or pacemakers, and particularly to programmable, rate-responsive pacemakers. More particularly, this invention relates to implantable cardiac pacemakers in which the sequential mode and/or various pacing parameters of the pacemaker are automatically and continually adjusted by the pacemaker to provide hemodynamically optimal pacing therapy.

BACKGROUND OF THE INVENTION

A pacemaker is an electronic, medical device that provides electrical pulses to stimulate a patient's cardiac tissues. Each electrical pulse causes depolarization of the stimulated cardiac tissue, thus causing a heart contraction.

Pacing therapy is used to relieve the symptoms associated with certain types of abnormal heart rhythms. For example, a pacemaker may be indicated when a patient suffers from bradycardia—a condition in which the patient's heart rate is slower than is physiologically acceptable. In such a patient, the electrical pulses provided by the pacemaker serve to regulate the patient's heartbeat at a more acceptable rate.

The earliest pacemakers provided stimulation pulses at a constant rate to a single chamber of a patient's heart. The paced rate, which was set at the time of implantation, was usually a rate appropriate for the patient while at rest. If the rate had to be changed surgery was required because physical access to the pacemaker was needed to change the paced rate. Modern pacemakers provide telemetry systems for remotely reading and changing the paced rate and other pacemaker parameters.

The cardiac rhythm of a healthy person varies as a function of the person's metabolic needs. For example, when exercising a person's heart rate normally increases to keep up with the increased demands placed on the body. Because early pacemakers provided stimulation pulses at a fixed rate, pacemaker patients might suffer from fainting or lightheadedness if they exerted themselves too strenuously.

Rate-responsive pacemakers improved on fixed rate pacemakers by altering the paced rate when physiologically indicated. Typically, a base heart rate, appropriate for the patient at rest, is maintained by the pacemaker. A physiological sensor generating a signal indicative of the patient's metabolic needs is monitored by the pacemaker, which when needed, increases the paced rate above the base rate. For example, during physical exertion, a patient's metabolic need is greater, and the heart rate should be increased accordingly.

Many rate-responsive pacemakers contain a mechanical transducer, such as a piezoelectric crystal, to monitor a patient's level of activity. The piezoelectric crystal provides an electrical output when subject to mechanical stresses, such as may occur due to a patient's body movements during physical exertion. Unfortunately, some piezoelectric sensors are susceptible to providing erroneous indications of activity when subjected to vibrations.

Alternatively, physiological sensors may be used that rely on changes in, or absolute measurements of, a physiological parameter to indicate metabolic need. Ideally, the monitored parameter is readily measurable, responds quickly to changes in metabolic need, and is largely immune to outside influences. Much effort has been, and continues to be, expended in developing effective techniques and sensors for indicating a patients metabolic need. Possible parameters which may be measured as an indication of metabolic need include a patient's central venous temperature or blood oxygen saturation. Other sensors and techniques are disclosed in copending, commonly assigned U.S. patent application Ser. No. 08/259,084, filed Jun. 13, 1994, which is herein incorporated by reference.

A signal from the mechanical and/or physiological sensor is analyzed by the pacemaker to determine the patient's metabolic need. If the sensor signal exceeds a predetermined threshold, the pacemaker may determine that the patient's metabolic need has increased and increase the pacing rate accordingly. Interpolating values from a look up table may be used to determine a rate change or delta to be applied to the current paced rate to achieve a rate suitable for the measured metabolic need. Similarly, when the sensor signal falls below the threshold, the pacemaker may reduce the paced heart rate to a level appropriate for the lower level of patient activity. Thus, rate-responsive pacing attempts to provide a paced heart rate which increases and decreases in a natural way depending on the physiological needs of the patient.

For example, a pacemaker patient may begin to walk up several flights of stairs. If the patient had a constant rate pacemaker, it would continue to pace the heart at the programmed rate—a rate that may be inappropriate for the patient's level of activity, resulting in lightheadedness or fainting. However, if the patient had a rate-responsive pacemaker, the increased exertion (relative to the patient's resting state) would be detected by the pacemaker and the pacing rate increased accordingly. Similarly, when the patient ceases climbing the stairs, the pacemaker returns to pacing at the base rate, possibly gradually reducing the rate over a period of several minutes. Thus, the paced heart rate increases and decreases according to the metabolic needs of the patient.

Another advance in pacemaker technology was the development of the "demand" pacemaker. A demand pacemaker has the ability to sense a patient's natural cardiac activity, and delivers a pacing pulse only in the absence of such activity. Demand pacemakers use sensing leads to monitor the patient's intracardiac electrogram ("IEGM") to detect spontaneous cardiac depolarizations. Pacing pulses are then only provided if a depolarization is not detected within a predetermined time interval following a previous depolarization (either natural, or paced). Providing pacing pulses only when needed decreases the power consumption of the pacemaker, thereby lengthening the useful life of the pacemaker's battery. Furthermore, sensing natural cardiac activity reduces the possibility of providing stimulation pulses during a heart's T-wave, which is otherwise known to cause fibrillation.

In a healthy heartbeat, atrial and ventricular contractions are temporally related in a way that provides increased cardiac output. A major benefit of dual-chamber or universal pacemakers is the capability of providing a pacing regime that closely approximates the natural synchrony between atrial and ventricular contractions. In patients with severely compromised cardiac performance, optimization of hemodynamic performance may be critical to successful pacing therapy. A significant number of patients, who suffer from hemodynamically compromised cardiac output associated with CHF or cardiomyopathy may benefit from optimal chronotropic pacemaker stimulation.

Furthermore, a growing body of clinical evidence suggests that for some patients having severely compromised cardiac output may show improved hemodynamic performance after several weeks or months of chronotropic pacing therapy. In particular, patients suffering from hypertrophic cardiomyopathy, hypertrophic obstructive cardiomyopathy, and dilated cardiomyopathy have shown significant improvements, and seem most responsive to short A-V delays.

The dual-chamber pacemaker has the capability of providing chronotropic pacing therapy. It uses two or more leads, and may be programmed to pace and/or sense both chambers of the heart. For example, the pacemaker may be programmed to sense natural P-wave activity in the atrium, and to pace in the ventricle (P-V pacing). A universal pacemaker provides the medical practitioner a wide range of possible pacing regimes to consider when instituting pacing therapy for a cardiac patient.

When programming a universal pacemaker, the physician is thus faced with programming heart rates for resting and active conditions, but also with programming the lengths of various refractory periods, the desired A-V delay to maintain A-V synchrony, and whether to pace and/or sense either one or both chambers. Selecting the optimal combination of parameters and modes may prove difficult, especially since optimal pacing parameters and modes vary from patient to patient, and possibly from one pacemaker model to the next.

Adding to the difficulty of programming an optimal pacing regime, is the fact that pacemakers are programmed in an "open loop" manner. In other words, there is no direct and continuing feedback relating changes in cardiac performance to changes in the pacing regime.

In a typical scenario, the pacemaker is programmed at implant. During post-implant follow up visits, the physician may reprogram the pacemaker based on medical testing, as well as on patient input. However, subsequent changes in a patients cardiovascular condition may affect hemodynamic efficiency so that the pacemaker's programming no longer provides optimal pacing therapy. Since there is no feedback relating to cardiac performance, such suboptimal pacing might not be detected.

Suboptimal pacing in some patients may not only deprive the patient of the short term benefits of optimal pacing, but also the long term improvement in hemodynamic performance suggested by some clinical testing. Because of the open-loop nature of tuning programmable parameters of a pacemaker, whether rate-responsive or universal, it is difficult, if not impossible, to ensure near optimal pacing therapy. Therefore, to provide optimal pacing therapy, a "closed-loop" way of adjusting pacing parameters and evaluating cardiac performance is needed.

SUMMARY OF THE INVENTION

The disadvantages and limitations of the previously known approaches for optimizing pacing therapy are overcome by the present invention. The invention is directed toward a pacemaker including a processing system that tests alternative pacing regimes, and monitors cardiac performance to automatically select an optimal pacing regime.

The pacemaker includes sensors for monitoring physiological parameters indicative of cardiac performance, and a processing system for testing alternative pacing regimes. The processing system analyzes changes in cardiac performance that correlate to changes in the pacing regime. Changes in the pacing regime that lead to improved cardiac performance are retained to define a new pacing regime to be used.

In a first embodiment of the pacemaker of the present invention, the pacing regime is defined by a set of programmable parameters. Such parameters may include, for example, atrial escape interval, A-V delay, or other pacing parameters which are known in the pacing art. Together, all of the possible combinations of parameters define a "parameter space", and includes all possible pacing regimes.

At implant, a medical practitioner programs the pacemaker choosing from the parameter space a selected "parameter set" that will provide satisfactory pacing therapy to the patient. Because of the difficulties faced by the practitioner in optimizing the parameter set, the processing system of the present invention searches the parameter space and selects a parameter set that results in optimal cardiac performance. The pacemaker searches the parameter space by introducing variations in the currently programmed parameter set, and sampling the corresponding cardiac performance. By "testing" many parameter sets over a period of time, the processing system is able to construct a performance surface relating hemodynamic performance to the parameters sets. A peak in the performance surface corresponds to maximum levels of hemodynamic performance; therefore, the parameter set corresponding to a maximum in the performance surface is an optimal parameter set. Having found such an optimal parameter set, the pacemaker replaces the parameter set currently being used by the pacemaker with the newly determined optimal pacing parameters. Because the parameter space is continually searched for the optimal parameter set, the pacemaker provides near optimal pacing therapy.

In another embodiment of the present invention, the processing system uses heuristic methods to search the parameter space for an optimal parameter set. For example, instead of taking and storing many samples from the parameter space to determine the performance surface, the processing system may use a hill climbing technique to locate a hemodynamically optimal parameter set. In a hill climbing technique, only a small number of parameter sets near the current parameter set are tested. From the results of the test, the processing system may determine which direction is uphill, i.e. what changes in the parameters will result in increased hemodynamic performance. By continually repeating the hill climbing process, the hemodynamically optimal parameter set will eventually be found and tracked by the processing system.

In a preferred embodiment of the present invention, an optimal "sequential mode of operation" of the pacemaker is also determined. A dual-chamber pacemaker can be programmed to operate in various modes to sense and/or pace either the atrium, the ventricle, or both. Depending on the condition of the patient's heart, one of the pacing modes may prove to be more optimal hemodynamically. For example, in a patient whose natural conduction time is too long, either paced atrium-paced ventricle or sensed atrium-paced ventricle may be appropriate, but one of these two sequential modes of operation may be more optimal hemodynamically. The processing system in the preferred embodiment of the pacemaker may determine the optimal sequential mode of operation (i.e. atrial pacing-ventricular pacing (A-V), atrial sensing-ventricular pacing (P-V), atrial pacing-ventricular sensing (A-R), or atrial sensing-ventricular sensing (P-R)) in addition to determining an parameter set that provides optimal cardiac output.

The optimal sequential mode of operation may be varied depending on a patient's level of activity. For example, in a patient suffering from chronotropic incompetence (the failure of heart rate to increase with exercise), an A-R sequential mode of operation may be appropriate for a resting state, whereas an A-V sequential mode of operation may be better while exercising. Therefore, in the preferred embodiment of the invention, multiple performance surfaces are determined—one surface for each level of a patient's activity.

Many methods may be used to determine a patient's activity level. For example, sensors for detecting body motion, cardiac wall motion (see, for example, U.S. Pat. No. 5,480,412 (Mouchawar), issued Jan. 2, 1996, which is herein incorporated by reference), or blood oxygen saturation, may be used as an "exercise" sensor. A low average sensor output might be used to identify a level of activity corresponding to a patient's normal awake activity level. A sudden drop in the sensor output would be indicative of a sleeping or resting patient, while a sudden increase would be indicative of an exercising patient.

Alternatively, sleep, wake, and exercise state may be determined by analyzing the statistical mode and variance of a patient's activity. During sleep, a patient's activity is low and shows little variation. However, while awake and while exercising, the variation in activity is much larger. Thus, by measuring the variation in a patient's activity, the patient's resting state may easily be determined.

By sensing the activity level as well as the cardiac performance of a patient, the preferred embodiment of the present invention may, automatically determine a hemodynamically optimal pacing regime, including automatically changing the pacemaker's sequential mode of operation.

BRIEF DESCRIPTION OF THE DRAWINGS

These and other aspects of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENT

Figure 1:
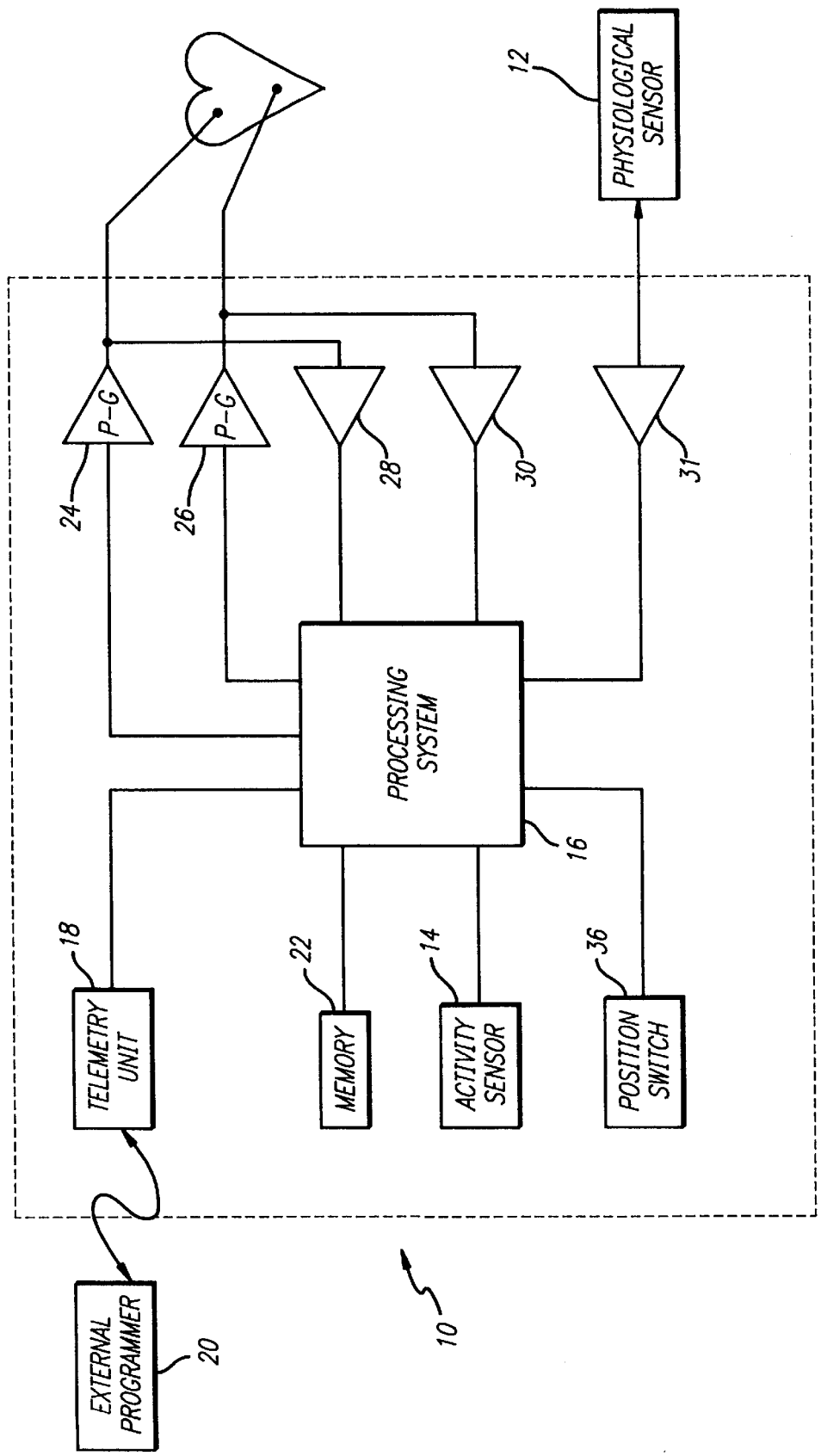
FIG. 1 is a block diagram of a dual-chamber pacemaker in accordance with principles of the present invention.

FIG. 1 is a block diagram of an exemplary dual-chamber implantable pacemaker 10 in accordance with the principles of the present invention. The pacemaker 10 operates to provide hemodynamically optimal pacing therapy to a patient. The pacemaker 10 uses a sensor 12 through signal processing circuit 31 to measure a physiological indication of cardiac performance. For example, the sensor 12 may measure mixed venous oxygen saturation, which is indicative of cardiac performance, as is discussed below. The pacemaker 10 preferably also has a sensor 14 for determining the patient's exercise need, and may comprise an activity sensor. Alternatively, the sensor 14 may be a cardiac wall motion sensor or accelerometer, as disclosed in copending commonly assigned U.S. patent application Ser. No. 08/259,084, filed Jun. 13, 1994, now U.S. Pat. No. 5,549,650 which is herein incorporated by reference.

Signals from the sensors 12 and 14 are received by the processor 16 and processed to select an hemodynamically optimal pacing regime. A pacing regime is defined by a set of pacing parameters which may be programmed by way of a telemetry module 18 and an external programmer 20. The pacing parameters are stored in a memory 22, and may include, but are not limited to: A-V interval and heart rate. As a result of the selected A-V interval and heart rate, a sequential mode of operation results.

Based on the signals from the sensors 12 and 14, the processor 16 retrieves a set of parameters from the memory 22, causing the pacing regime defined by the selected parameter set to be implemented.

The dual-chamber pacemaker 10 also includes pulse generating circuitry 24 and 26, cardiac monitoring circuitry 28 and 30, and two conventional pacing leads 32 and 34. The pacing leads 32 and 34 deliver pacing pulses generated by the pulse generators 24 and 26 to a patient's cardiac tissue; typically to the right atrium and ventricle, respectively. The pacing leads 32 and 34 may also be used to monitor natural, cardiac electrical activity to inhibit pacing if the patient's natural cardiac rhythm is metabolically sufficient.

The pacemaker 10 may also include a position switch 36 to monitor whether a patient is supine or upright. For example, the switch 36 may be a mercury switch, an accelerometer, or other conventional sensor that senses a patient's orientation, or perhaps an accelerometer that is directionally sensitive and aligned along a fixed plane relative to the patient's body. Such information may be useful in determining if the patient is sleeping. Additionally, an activity monitor (e.g., within the processing system 16) may be incorporated into the pacemaker 10 to provide an indication of a patient's degree of physical activity. For an example of an activity monitoring system, see U.S. Pat. No. 5,476,483 (Bornzin), issued Dec. 19, 1995, which is herein incorporated by reference.

Referring again to FIG. 1, the manner by which the pacemaker 10 delivers pacing therapy is controlled by the processor 16 in accordance with parameters stored in the memory 22. Many of these parameters are known in the art (i.e., escape interval, refractory period, etc.), and they may be programmed by a medical practitioner using the programmer 20 that communicates with the processor 16 through the telemetry circuit 18.

However, static parameters stored in the memory 22 do not provide the processor 16 with all of the information necessary to control the manner by which therapies are administered. Rather, it is necessary for the processor 16 to receive information pertaining to the patient's current cardiac condition in order to optimize hemodynamic performance, so that the patient receives optimal chronotropic stimulation from the implantable cardiac stimulating device.

Although the processor 16 may be programmed by a medical practitioner via the telemetry circuit 18 to operate in one of several modes, one of the advantages of the present invention is that the processor 16 can fine tune the parameters set by the practitioner to achieve hemodynamically optimal performance. For example, the processor 16 may be initially programmed to establish a given A-V interval in the patient. The processor 16 may then dynamically adjust the A-V interval based on the determination of current cardiac performance, as measured by stroke volume, ejection period, contractility, or some other measurable indicator of cardiac performance.

In one illustrative embodiment of the invention, the physiological sensor 12 measures changes in mixed venous blood oxygen content to assess hemodynamic performance. Cardiac output, which is the product of heart rate and stroke volume, is related to venous oxygen content by the Fick equation:

$$VO_2 >> (Hr)(SV)(1.34 \times Hgb)(SaO_2 - SVO_2) \qquad (1)$$

where $VO_2$ is oxygen consumption, Hr is heart rate (bpm), SV is stroke volume (liters/beat), 1.34 is the $O_2$ carrying capacity of Hemoglobin (liters/kg), Hgb is the Hemoglobin content of blood (kg/liter), and $(SaO_2-SVO_2)$ is the difference between the fractional arterial and mixed venous oxygen saturations.

Typically, $VO_2$, Hgb, and $SaO_2$ do not change significantly over periods of up to several minutes. Consequently, changes in SV and heart rate (i.e., cardiac output) effect the $SVO_2$ level. An increase in cardiac output, (Hr)(SV), causes a reduction in the difference between the arterial and mixed venous oxygen saturations, $(SaO_2-SVO_2)$. Since arterial oxygen saturation is relatively constant for short periods, the reduced difference in oxygen saturation may be attributed to an increased mixed venous oxygen saturation. Therefore, over short periods of time, changes in $SVO_2$ are indicative of changes in cardiac output.

A pacemaker in accordance with the principles of the present invention may therefore use changes in mixed venous oxygen saturation to optimize hemodynamic performance by increasing cardiac output. Specifically, such a pacemaker may test alternative pacing parameters by temporarily altering one or more of the pacing parameters by a small amount and measuring the change in $SVO_2$. Increases in $SVO_2$ would indicate the altered parameters correspond to an increased cardiac output, whereas a decrease in $SVO_2$ would indicate reduced cardiac output.

Figure 2:
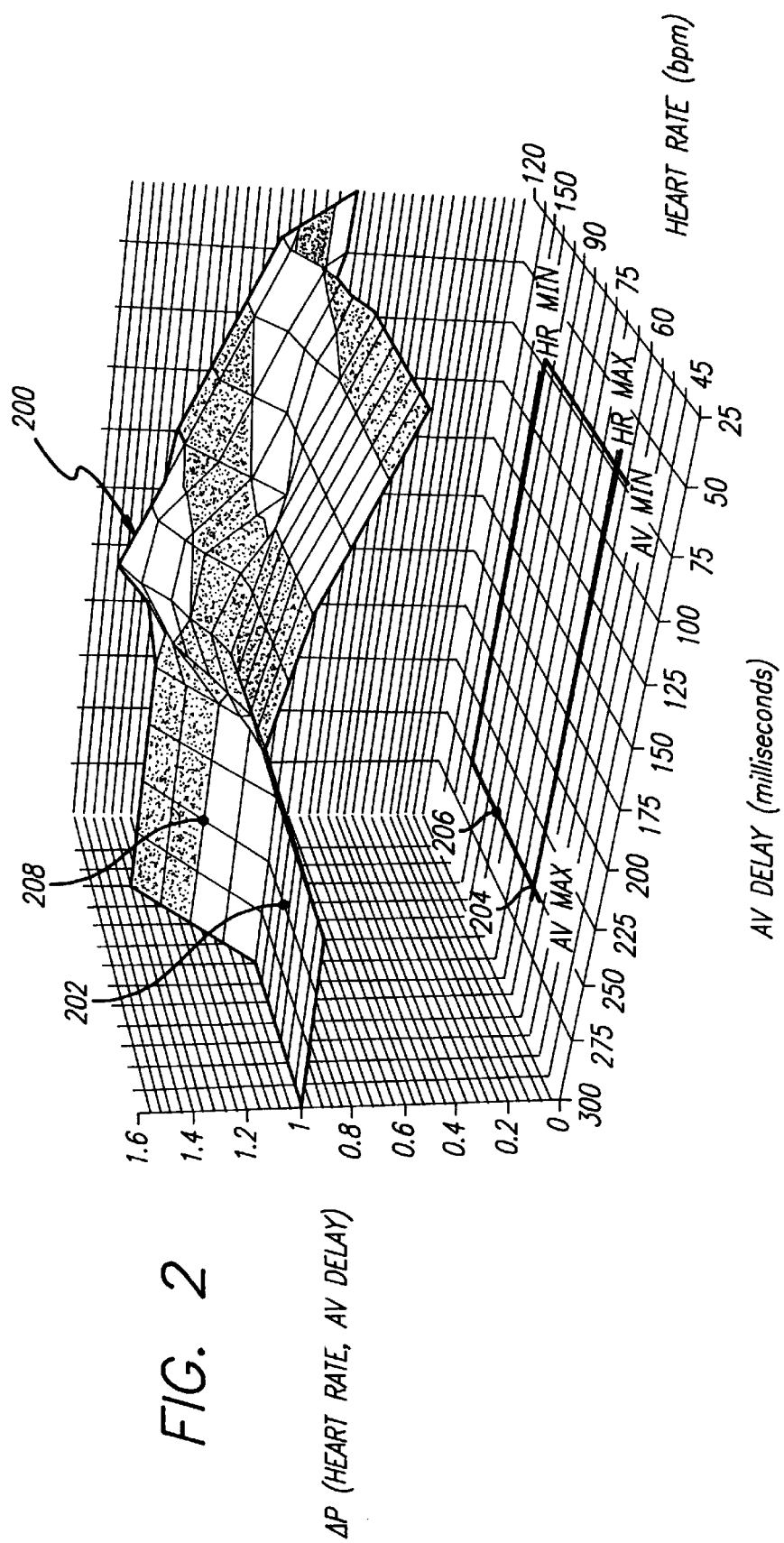
FIG. 2 is a three-dimensional graph illustrating the effect small changes in various pacing parameters have on hemodynamic performance.

By repeatedly testing various parameter sets, a performance surface, or matrix, relating cardiac performance to the pacing parameters is created. FIG. 2 is a hypothetical performance surface relating normalized changes in cardiac performance ($\Delta P$) to heart rate and A-V delay interval. The performance surface may be analyzed to determine the parameter set that maximize hemodynamic performance. The performance maximizing parameter set are then selected as the new pacing regime.

Since, the optimal pacing regime may differ for a patient when engaged in a physical activity relative to the patient at rest, the pacemaker of FIG. 1 may measure multiple performance surfaces, each corresponding to a different level of patient activity. Various sensors, such as cardiac wall motion sensors, piezoelectric motion sensors, accelerometers, or blood oxygen saturation sensors, may be used to determine a patient's activity level.

Figure 4:
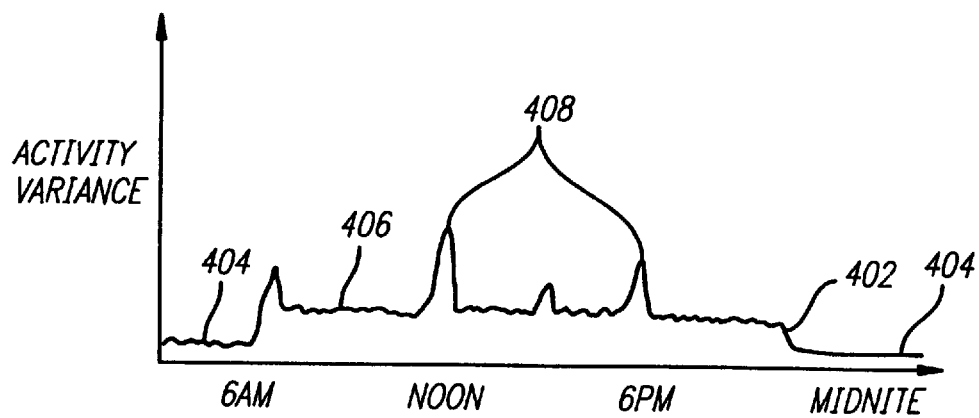
FIG. 4 is the processed output signal of an activity sensor over a 24 hour period, which provides an indication of activity variance during sleeping, waking, and exercising states.

The processed output signal of such an activity sensor is shown in FIG. 4, and provides an indication of activity variance which can be used to distinguish between sleeping, waking, and exercising states. The output signal processed to derive activity variance is described in U.S. Pat. No. 5,476,483, supra. For example, while sleeping (i.e., at profound rest), the activity variance signal from the activity variance exhibits a marked drop 402, followed by an extended period at a low signal level 404. A "wake state" may be determined by a low average signal level 406, while an "exercise state" is easily detected by sudden increases 408 in the activity variance signal.

Figure 5:
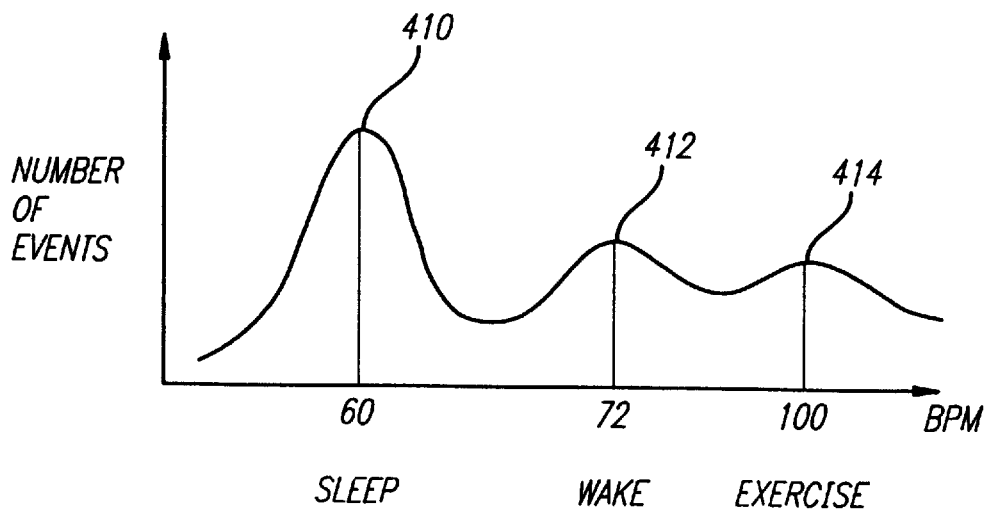
FIG. 5 depicts an illustrative activity variance histogram to identify three statistical modes, or states, corresponding to sleep, wake, and exercise.

Briefly, the activity variance may be monitored and analyzed statistically in the form of a histogram to identify three statistical modes, or states, corresponding to sleep, wake, and exercise, as illustrated in FIG. 5. During sleep, activity variance is usually low, corresponding to mode 410. Conversely, while awake, activity variance shows a second and third mode, and the wake and exercise states can be distinguished by relatively moderate (at 412) and high variance (at 414), respectively.

Referring now to FIG. 2, an exemplary performance surface 200 relating normalized cardiac output to changes in heart rate and A-V delay is shown. For a complete description of the cardiac performance surface, or matrix, see U.S. Pat. No. 5,549,650 (Bornzin et al.), issued Aug. 27, 1996, which reference is hereby incorporated herein by reference.

Briefly, FIG. 2 shows a three-dimensional representation of the cardiac performance surface, $\Delta P$(Heart Rate, AV Delay). A first axis is defined by AV-delay (AV), which varies from $AV_{MIN}$ of 75 milliseconds to $AV_{MAX}$ of 250 milliseconds. A second axis is defined by heart rate (HR), which varies from $HR_{MIN}$ of 65 beats per minute to $HR_{MAX}$ of 100 beats per minute. The third axis represents the value for cardiac performance for each given AV/HR pair, and is the value which is stored in each cell of the cardiac performance surface. A performance value of 1.0 for a given parameter set may indicate cardiac performance that is unchanged relative to the currently selected parameter set. A performance value greater than 1.0 may indicate improved cardiac performance, while a value less than 1.0 may indicate decreased cardiac performance.

For example, a first point 202 on the performance surface 200 corresponds to a parameter set 204 in the parameter space. The parameter set defined by the point 204 includes a heart rate of 65 beats-per-minute (bpm) and an A-V delay of 250 milliseconds (ms). While a second point 208 on the performance surface 200, corresponding to parameter set 206 in the parameter space may result when the heart rate is increased to 90 bpm, with the A-V delay held at 250 ms.

In a preferred embodiment of the invention, multiple performance surfaces are used, each one corresponding to a level of activity of the patient. For example, a first performance surface may be used to determine optimal pacing parameters while the patient is at sleep (or profound rest), and another performance surface for when the patient's activity level exceed a predetermined threshold. In the extreme, a continuum of performance surfaces (i.e., a performance volume) may be determined, and the optimum pacing parameters selected continually based on the patient's prevailing level of activity (i.e., at sleep, wake, or physical exertion).

Figure 3:
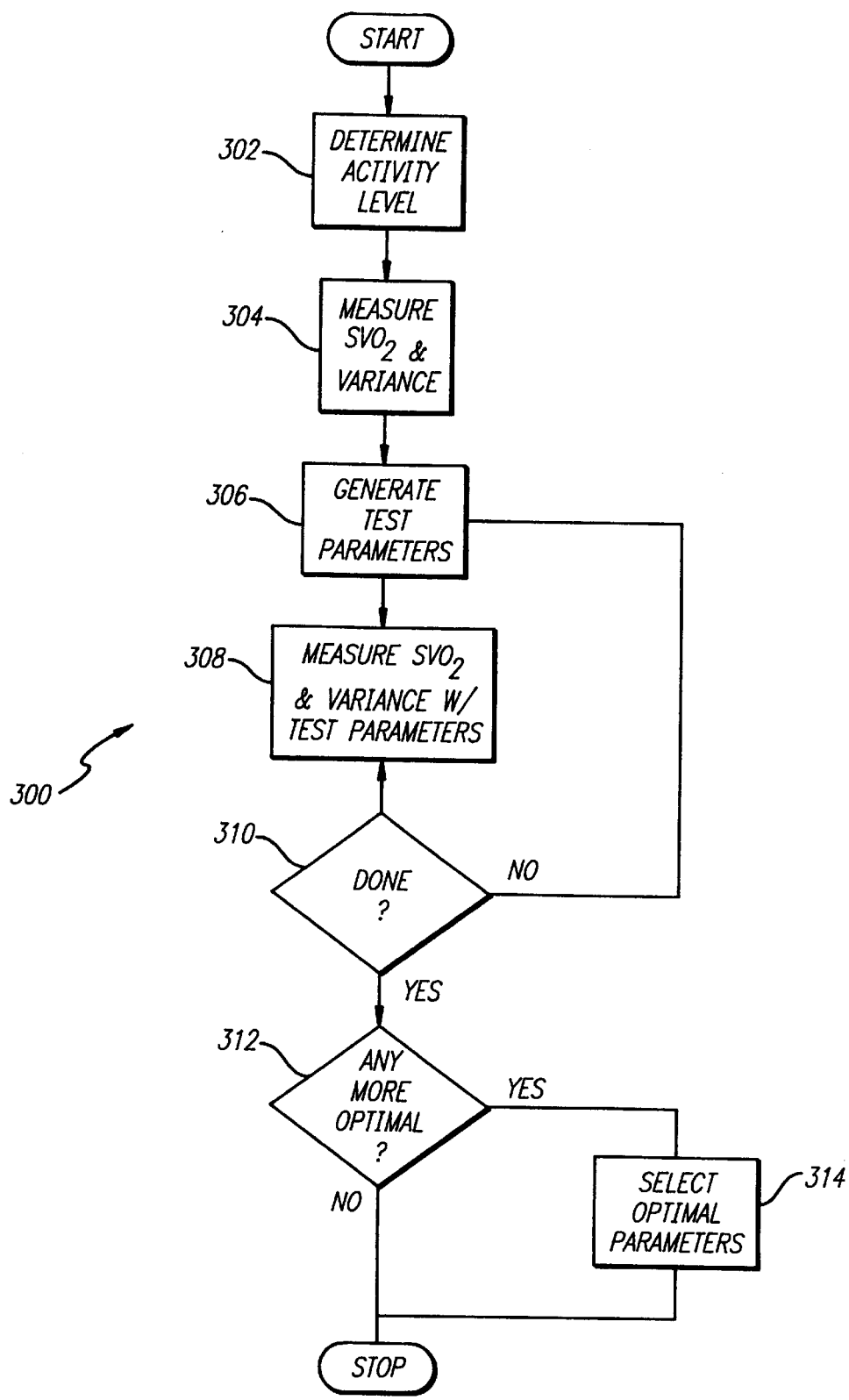
FIG. 3 is a logic flow diagram showing how the system of the present invention adjusts heart rate and A-V delay to optimize cardiac output.

Referring now to FIG. 3, a logic flow diagram 300 illustrating the cardiac performance optimizing algorithm is described. The routine outlined in FIG. 3 is triggered on a periodic basis, determined either by the elapse of a certain time interval, or the existence of certain predetermined conditions. For example, the optimizing routine may be invoked by a timer once ever hour, so that 24 points on the performance surface are sampled every day. Longer or shorter intervals may be used depending on the patient's condition.

Alternatively, the optimization routine may be activated in response to a certain condition. For example, the routine may be invoked whenever there is a significant change in the patient's level of activity. This ensures that some parameter testing will be accomplished while the patient is exercising, as well as while at rest. In another embodiment, a combination of timed intervals and changes in activity might be used, thus ensuring testing during periods of exercise even if the exercise period does not include a regularly scheduled parameter test.

At step 302 of FIG. 3, the activity level of the patient is determined. Various parameters which may be measured to determine the activity level. For example, if the measured activity variance is below a predetermined threshold, it indicates the patient is sleeping.

Once the activity level is determined, the mixed venous oxygen saturation, $SVO_2$, and its variance, are measured at step 304 while using the current pacing regime. The $SVO_2$ variance may be estimated by several methods. One method of estimating the variance involves taking the absolute value of the difference in $SVO_2$ levels measured several heartbeats apart, and averaging the differences.

After establishing the starting value of $SVO_2$, the pacing regime is changed, by altering the pacing parameters to some testing values at step 306. $SVO_2$ and its variance are measured while using the test parameters (308), so that the effects of the test parameters may be determined relative to the previously set parameters.

For safety reasons, the test parameters may be restricted to a certain range of values. For example, in FIG. 2, A-V delay has been limited to a range of 75 to 250 milliseconds, ($AV_{min}$ and $AV_{max}$, respectively). Similarly, minimum and maximum heart rates ($HR_{min}$ and $Hr_{max}$, respectively) have been established, so that testing values are restricted to the area within a box 202 of FIG. 2.

Steps 306 and 308 are repeated many times to establish the shape of the performance surface. The testing may be performed in any number of ways. For example, each invocation of the optimizing routine 300 may cause just one set of test parameters to be tested. Alternatively, each invocation of the optimization routine may test a small number of different test parameters.

Once it is determined at test 310 that the performance surface has been established, the surface is analyzed at test 312 to determine which set of testing parameters give the greatest increase (if any) in cardiac performance, as measured by change in $SVO_2$, over the performance associated with the currently selected parameters. The parameter set having the highest level of cardiac performance is then set as the current pacing regime at step 314.

To prevent unnecessary changes in pacing regime, the measured change in mixed venous oxygen saturation should be compared with its variation as determined in step 308. If the measured change is significant compared to the natural variation, then the pacing regime should be changed; otherwise, if the measured change is within the range of variation in $SVO_2$, then the current pacing regime is retained.

Testing for statistical significance may involve repeated tests to determine the mean and variance of $SVO_2$. Because the processing power of control system 26 may be limited, simplified estimators should be used to keep calculations to a minimum.

The selection of test values for the pacing parameters may be selected to provide exhaustive coverage of the parameter space. This entails keeping track of which parameter combinations have been tested, and iterating over all possible parameter values. Exhaustive coverage requires a larger memory to store the test results corresponding to each combination of test parameters. However, exhaustive coverage has the advantage of ensuring that a globally optimum set of parameters will be detected.

Alternatively, a hill climbing heuristic may be implemented so that only a limited number of test parameter set are actually tested. In essence, test parameters are selected from the neighborhood of the current parameters. If the results of a particular set of test parameters shows an improvement in cardiac performance, additional parameter sets are tested from those in the vicinity of the set that showed improvement. Hill climbing techniques reduce the amount of memory required to search the performance surface for the optimum value, but may get stuck at a locally optimum set of parameters, and therefore not select the globally optimum pacing regime.

The process described in the flow chart shown in FIG. 3 may be repeated for each level of activity, for example, during sleep, while the patient's awake, and during exercise. This requires searching the performance surface for the optimal set of parameters associated with each given level of activity. This would allow the patient to be paced using the optimal parameter set associated with each level of activity. This allows the pacemaker to provide optimal pacing therapy in a "closed-loop" fashion by adjusting pacing parameters and evaluating cardiac performance on a continuous basis, while optimizing pacing for each level of activity.

The preceding discussion has focused on the use of mixed venous oxygen saturation as an indicator of cardiac performance. Many other physiological measurements may be used instead of, or in addition to, $SVO_2$ in estimating cardiac performance. For example, right or left ventricular blood pressure, the output of a cardiac accelerometer (see U.S. patent application Ser. No. 08/259,084 (Bornzin et al.), filed Jun. 13, 1994, now U.S. Pat. No. 5,549,650 or blood flow measurements, may be used in an manner analogous to that described to determine an optimal pacing regime.

One skilled in the art will thus appreciate that the present invention can be practiced by other than the described embodiments, which are presented for purposes of illustration and not of limitation, and that the present invention is limited only be the claims which follow.

What is claimed is:

1. A cardiac pacemaker for providing optimal pacing therapy to a patient, the pacemaker having a plurality of pacing modes, the pacemaker comprising:

first sensing means for providing a signal indicative of cardiac performance;

pulse generating means for generating stimulation pulses to a patient's heart;

exercise detecting means for detecting the exercise state of a patient;

means for determining when the cardiac performance is maximized based on the first sensing means;

processing means for controlling the pulse generating means to operate in the plurality of pacing modes and for determining an optimal pacing mode when the determining means indicates that the cardiac performance is maximized for a current exercise state of the patient; and means for automatically switching from a current pacing mode to the optimal pacing mode.

2. The pacemaker as recited in claim 1, wherein the pacemaker has a plurality of pacing parameters, wherein the processing means comprises:

means for determining an optimal set of pacing parameters in each pacing mode by adjusting a plurality of pacing parameters until a maximum cardiac performance is obtained;

means for comparing the maximum cardiac performance in each pacing mode; and means for selecting as the optimal pacing mode that pacing mode which has the maximum cardiac performance.

3. The pacemaker as recited in claim 2, wherein the means for determining the optimal set of pacing parameters comprises:

means for periodically generating a plurality of temporary pacing parameters and for measuring a plurality of changes in cardiac performance as indicated by the first sensor;

means for analyzing the changes in cardiac performance to determine if cardiac performance is improved using any of the plurality of temporary pacing parameters; and means for adjusting a current set of pacing parameters to an optimal set of the plurality of temporary pacing parameters if cardiac performance is improved.

4. The pacemaker as recited in claim 1, wherein:

the plurality of pacing modes includes an A-V sequential mode;

the processing means includes means for determining an optimal A-V sequential pacing mode; and the pulse generating means includes means for generating stimulation pulses in the optimal A-V sequential pacing mode.

5. The pacemaker as recited in claim 4, wherein the means for determining the optimal A-V sequential pacing mode comprises:

means for defining a plurality of A-V sequential pacing modes;

means for determining an optimal set of pacing parameters for each of the plurality of A-V sequential pacing modes;

means for comparing the maximum cardiac performance in each pacing mode using the optimal set of pacing parameters; and means for selecting as the optimal A-V sequential pacing mode that A-V sequential pacing mode which provides a maximum cardiac performance.

6. The pacemaker as recited in claim 5, wherein the A-V sequential modes have a programmable A-V delay and rate, wherein the means for defining a plurality of A-V sequential pacing modes comprises means for controlling the A-V delay and the rate so that one of:

an atrial pacing/ventricular pacing (A-V) mode, an atrial sensing/ventricular pacing (P-V) mode, an atrial pacing/ventricular sensing (A-R) mode, or an atrial sensing/ventricular sensing (P-R) mode is enabled.

7. The pacemaker as recited in claim 1, wherein:

the exercise detecting means comprises means for detecting a plurality of exercise levels of the patient; and the means for determining an optimal sequential mode of operation further comprises means for determining an optimal pacing mode for the patient at each of the plurality of exercise levels.

8. The pacemaker as recited in claim 1, wherein:

the exercise detecting means includes means for detecting when the patient is in one of a rest state, a wake state, or an exercise state; and the processing means for determining the optimal pacing mode further includes means for determining an optimal pacing mode while the patient is in one of the rest state, the wake state, or the exercise state.

9. A method of providing hemodynamically optimum pacing therapy in an implantable stimulation device having a plurality of pacing modes, comprising the steps of:

sensing a signal indicative of cardiac performance;

detecting the exercise state of a patient;

generating stimulation pulses with a pulse generator to a patient's heart;

controlling the pulse generator to operate in the plurality of pacing modes;

determining an optimal pacing mode when the cardiac performance is maximized while the patient is in a current exercise state; and automatically switching from a current pacing mode to the optimal pacing mode when cardiac performance is improved by a prescribed amount.

10. The method as recited in claim 9, wherein the implantable stimulation device has a plurality of pacing parameters, wherein the step of determining the optimal pacing mode comprises the steps of:

determining an optimal set of pacing parameters in each of the plurality of pacing modes by adjusting a plurality of pacing parameters until a maximum cardiac performance is obtained; comparing the maximum cardiac performance in each pacing mode; and selecting as the optimal pacing mode that pacing mode which has the maximum cardiac performance.

11. The method as recited in claim 10, wherein the step of determining the optimal set of pacing parameters comprises the steps of:

periodically generating a plurality of temporary pacing parameters;

measuring a plurality of changes in cardiac performance;

determining if cardiac performance is improved using any of the plurality of temporary pacing parameters; and adjusting a current set of pacing parameters to an optimal set of the plurality of temporary pacing parameters if cardiac performance is improved.

12. The method as recited in claim 9, wherein:

the plurality of pacing modes includes an A-V sequential mode;

the step of determining the optimal pacing mode comprises the step of determining an optimal A-V sequential pacing mode; and the step of generating stimulation pulses comprises the step of generating stimulation pulses in the optimal A-V sequential pacing mode.

13. The method as recited in claim 12, wherein the step of determining the optimal A-V sequential pacing mode comprises the steps of:

defining a plurality of A-V sequential pacing modes;

determining an optimal set of pacing parameters for each of the plurality of A-V sequential pacing modes;

comparing the maximum cardiac performance in each pacing mode using the optimal set of pacing parameters; and selecting as the optimal A-V sequential pacing mode that A-V sequential pacing mode which provides a maximum cardiac performance.

14. The method as recited in claim 13, wherein the A-V sequential modes have a programmable A-V delay and rate, wherein the step of defining a plurality of A-V sequential pacing modes comprises the step of controlling A-V delay and rate so that one of:

an atrial pacing/ventricular pacing (A-V) mode, an atrial sensing/ventricular pacing (P-V) mode, an atrial pacing/ventricular sensing (A-R) mode, or an atrial sensing/ventricular sensing (P-R) mode is enabled.

15. The method as recited in claim 9, wherein:

the exercise detection means comprises means for detecting a plurality of exercise levels of the patient; and the step for determining an optimal sequential mode of operation further comprises the step of determining an optimal pacing mode for the patient at each of the plurality of exercise levels.

16. The method as recited in claim 9, further comprising the steps of:

detecting when the patient is in one of a rest state, a wake state, or an exercise state; and determining an optimal pacing mode while the patient is in one of the rest state, the wake state, or the exercise state.

17. A dual-chamber implantable stimulation device, comprising:

atrial sensing means for sensing P-waves;

ventricular sensing means for sensing R-waves;

timing means for controlling an atrial escape interval and an A-V time interval;

pulse generator means for generating an atrial stimulation pulse (A-pulse) in the absence of a sensed P-wave within the atrial escape interval, and a ventricular stimulation pulse (V-pulse) in the absence of an R-wave within the A-V time interval;

sensing means for sensing a signal representative of hemodynamic performance;

exercise detection means for detecting a patient's level of exercise corresponding to at least one of a rest state, a wake state, or an exercise state;

means for determining an optimal sequential mode of operation corresponding to maximum hemodynamic performance based on the patient's level of exercise; and means for adjusting the pulse generator means to generate stimulation pulses in the optimal sequential mode of operation.

18. The dual-chamber implantable stimulation device as recited in claim 17, wherein:

the sequential mode of operation comprises one of an atrial pacing/ventricular pacing (A-V) mode, an atrial sensing/ventricular pacing (P-V) mode, an atrial pacing/ventricular sensing (A-R) mode, or an atrial sensing/ventricular sensing (P-R) mode.

19. The implantable dual-chamber stimulation device as recited in claim 17, wherein the means for determining an optimal sequential mode of operation comprises:

means for determining an optimal atrial escape interval; and means for determining an optimal atrial contraction-to-ventricular contraction time interval.

20. The dual-chamber implantable stimulation device as recited in claim 19, wherein the means for determining the optimal sequential mode of operation corresponding to the rest state comprises:

means for determining the patient's typical rate over a period of time corresponding to the rest state; and means for adjusting the atrial contraction-to-ventricular contraction time interval until a maximum hemodynamic performance is determined.

21. The dual-chamber implantable stimulation device as recited in claim 20, further comprising:

means for detecting a period of time corresponding to the rest state.

22. The dual-chamber stimulation device as recited in claim 20, further comprising:

means for determining an initial rate based on the patient's level of exercise; and means for adjusting the atrial contraction-to-ventricular contraction time interval until the maximum performance is determined.

23. The dual-chamber implantable stimulation device as recited in claim 22, wherein the means for determining the initial rate based on the level of exercise of the patient, further comprises:

means for rapidly adjusting the atrial escape interval based on the exercise level detection means until a steady state of exercise is achieved; and means for fine tuning the atrial escape interval for the maximum hemodynamic performance as sensed by the sensing means once steady state of exercise is achieved.

24. The dual-chamber implantable stimulation device as recited in claim 22, wherein the means for determining the initial rate based on the level of exercise of the patient, further comprises:

means for re-adjusting the atrial escape interval for the maximum hemodynamic performance after the adjusting means adjust the A-V delay for maximum hemodynamic performance.

* * * * *